United States Patent [19]

Hutton et al.

[11] Patent Number: 5,446,165
[45] Date of Patent: Aug. 29, 1995

[54] CRYSTALLINE 1-ALKYL-2-QUINOLINIUM SALTS

[75] Inventors: Jonathan Hutton, Adlington; David Waterson, Bollington, both of England

[73] Assignees: Zeneca Limited, London, England; Zeneca Pharma, Cergy Cedex, France

[21] Appl. No.: 107,147

[22] Filed: Aug. 17, 1993

Related U.S. Application Data

[62] Division of Ser. No. 802,614, Dec. 5, 1991, Pat. No. 5,260,442.

[30] Foreign Application Priority Data

Dec. 14, 1990 [EP]  European Pat. Off. ............ 90403609

[51] Int. Cl.$^6$ ........................................... C07D 405/12
[52] U.S. Cl. ..................................... 546/152; 546/182
[58] Field of Search ............... 546/157, 181, 182, 152

[56] References Cited

U.S. PATENT DOCUMENTS

| | | | |
|---|---|---|---|
| 1,941,312 | 12/1933 | Miescher et al. | 546/147 |
| 3,661,917 | 5/1972 | Kaiser et al. | |
| 3,743,737 | 7/1973 | Kaiser et al. | |
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/304 |
| 4,725,619 | 2/1986 | Chakraborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |
| 4,876,346 | 10/1989 | Musser et al. | 546/172 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/311 |
| 5,089,495 | 2/1992 | Crawley et al. | 514/253 |
| 5,089,513 | 2/1992 | Bird et al. | 514/365 |
| 5,098,930 | 3/1992 | Edwards | 514/259 |
| 5,098,932 | 3/1992 | Hamon | 514/462 |
| 5,105,020 | 4/1992 | Girodeau | 568/633 |
| 5,126,365 | 6/1992 | Bird | 514/451 |
| 5,132,328 | 7/1992 | Girodeau | 514/716 |
| 5,134,148 | 7/1992 | Crawley et al. | 546/153 |
| 5,179,115 | 1/1993 | Bruneau et al. | 514/387 |
| 5,202,326 | 4/1993 | Crawley et al. | 546/181 |
| 5,208,259 | 5/1993 | Bird et al. | 514/460 |
| 5,217,969 | 6/1993 | Bruneau et al. | 514/230.5 |
| 5,217,978 | 6/1993 | Bird | 514/312 |
| 5,221,677 | 6/1993 | Crawley et al. | 514/309 |
| 5,225,438 | 7/1993 | Dowell et al. | 514/459 |
| 5,232,930 | 8/1993 | Kingston et al. | 514/314 |
| 5,236,948 | 8/1993 | Waterson | 514/459 |
| 5,240,941 | 8/1993 | Bruneau | 514/312 |

FOREIGN PATENT DOCUMENTS

| | | |
|---|---|---|
| 0110405 | 6/1984 | European Pat. Off. |
| 0181568 | 5/1986 | European Pat. Off. |
| 0190722 | 8/1986 | European Pat. Off. |
| 0200101 | 12/1986 | European Pat. Off. |
| 0271287 | 6/1988 | European Pat. Off. |
| 0349062 | 6/1989 | European Pat. Off. |
| 385662 | 9/1990 | European Pat. Off. |
| 073783 | 7/1979 | Japan ............ 546/157 |

*Primary Examiner*—Donald G. Daus
*Attorney, Agent, or Firm*—Cushman Darby & Cushman

[57] ABSTRACT

The invention concerns quinolinium salt intermediates of the formula I

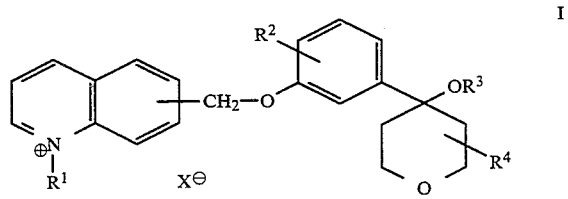

and processes for their manufacture; and their use in the manufacture of aryloxymethyl-substituted 1-alkyl-2-quinolone derivatives which are 5-lipoxygenase inhibitors.

3 Claims, No Drawings

CRYSTALLINE 1-ALKYL-2-QUINOLINIUM SALTS

This is a division of application No. 07/802,614, filed Dec. 5, 1991, U.S. Pat. No. 5,260,442.

The invention relates to chemical intermediates and, more particularly, it relates to quinolinium salt intermediates which are useful in the manufacture of certain aryloxymethyl-substituted 1-alkyl-2-quinolone derivatives which are inhibitors of the enzyme 5-lipoxygenase (hereinafter 5-LO). The invention also relates to processes for the manufacture of said quinolinium salt intermediates and to processes for the manufacture of said aryloxymethyl-substituted 1-alkyl-2-quinolone derivatives utilising said intermediates.

In European Patent Application No. 0385662 A2 (corresponding to U.S. Pat. No. 5,134,148) there are disclosed the structures of certain heterocycles which are effective as inhibitors of the enzyme 5-LO and processes for their manufacture. The disclosure includes information relating to the manufacture of certain 3-, 5-, 6- and 7-aryloxymethyl-substituted 1-alkyl-2-quinolone derivatives. Thus, for example, data within Examples 1, 2, 6, 7, 8, 11, 12 and 16-22 relate to such derivatives. These derivatives are manufactured by multi-step procedures which generally require several chromatographic purifications of various intermediates and, in particular, involve chromatographic purificaton of the final products.

We have now discovered a convenient and useful alternative process for the manufacture of said 1-alkyl-2-quinolone derivatives which significantly reduces the number of chromatographic purifications and, in particular, removes the need for chromatographic purification of the final products. The process makes use of novel crystalline 1-alkylquinolinium salts which may be transformed into the desired 1-alkyl-2-quinolone derivatives by oxidative procedures.

It will be appreciated that the selection of the anion portion of the quinolinium salt is important and that some anions more readily give crystalline salts than others. Thus, for example, it has been discovered that, for example, methyl 4-toluenesulphonate does not readily give a crystalline quinolinium salt on reaction with an appropriate quinoline. In addition it has been discovered that, although quinolinium salts may be formed by the reaction of an appropriate quinoline and an inorganic acid such as hydrochloric, hydrobromic or sulphuric acid, the acidity of the reaction conditions may, at elevated temperatures and depending upon the nature of the substituents on the quinoline ring, result in some degradation of the starting material. We have now discovered that such difficulties may be overcome if appropriate salts are prepared.

Accordingly to the invention there is provided a quinolinium salt of the formula I (set out hereinafter) wherein $R^1$ and $R^3$, which may be the same or different, each is (1–4C)alkyl;

$R^2$ is hydrogen or fluoro;

$R^4$ is hydrogen or (1–4C)alkyl; and $X^\ominus$ is bromide, iodide or (1–4C)alkyl sulphate.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

Suitable values for the generic terms referred to above include those set out below.

A suitable value for $R^1$, $R^3$ or $R^4$ when it is (1–4C)alkyl is for example, methyl, ethyl, propyl or butyl.

A suitable value for $X^\ominus$ when it is (1–4C)alkyl sulphate is, for example, methyl sulphate, ethyl sulphate or propyl sulphate.

A suitable position for the location of the aryloxymethyl substituent on the quinolinium ring is at the 3-, 5-, 6- or 7-position, preferably at the 3- or 6-position.

A preferred intermediate of the invention comprises a quinolinium salt of the formula II wherein $R^1$ is methyl or ethyl; $R^2$ is hydrogen or fluoro; $R^3$ is methyl; $R^4$ is hydrogen or methyl; and $X^\ominus$ is iodide or methyl sulphate.

A specific preferred intermediate of the invention is, for example, 6-[(3-fluoro-5-[4-methoxy-3,4,5,6-tetrahydro-2H-pyran-4-yl]phenoxy)methyl]-1-methyl-quinolinium iodide or 6-[(3-fluoro-5-[4-methoxy-3,4,5,6-tetrahydro-2H-pyran-4-yl]phenoxy)methyl]-1-methyl-quinolinium methyl sulphate.

According to a further feature of the invention there is provided a process for the manufacture of a quinolinium salt of the formula I which comprises the reaction of a quinoline derivative of the formula III wherein $R^2$, $R^3$ and $R^4$ have any of the meanings defined hereinbefore, with an alkylating agent of the formula $R^1$-X wherein $R^1$ has the meaning defined hereinbefore and X is bromo, iodo or (1–4C)alkyl sulphate.

A suitable value for X when it is (1–4C)alkyl sulphate is any of the suitable values defined hereinbefore for $X^\ominus$ when it is (1–4C)alkyl sulphate.

The reaction is conveniently performed in a suitable inert solvent or diluent, for example toluene, methylene chloride, chloroform, acetonitrile, ethyl acetate or butyl acetate, and at a temperature in the range, for example, $-10°$ to $+120°$ C. Preferably the reaction is performed using toluene or methylene chloride as solvent or diluent and at a temperature in the range, for example, 20° to 70° C.

The starting material of the formula III may be obtained by standard procedures of organic chemistry. The preparation of examples of such starting materials is described within European Patent Application No. 0385662 A2 (corresponding to U.S. Pat. No. 5,134,148). Thus, for example, it is disclosed therein that a starting material of the formula III may be prepared by the coupling reaction of a compound of the formula IV wherein Z is a displaceable group, with a phenol of the formula V.

A suitable displaceable group Z is, for example, a halogeno or sulphonyloxy group such as a chloro, bromo, iodo, methanesulphonyloxy or toluene-4-sulphonyloxy group.

Conveniently the coupling reaction may be carried out in the presence of a suitable base, for example, an alkali or alkaline earth metal carbonate, hydroxide, (1–4C)alkoxide or hydride, for example sodium carbonate, potassium carbonate, sodium hydroxide, potassium hydroxide, sodium methoxide, sodium ethoxide, sodium tert-butoxide, potassium tert-butoxide, sodium hydride or potassium hydride. The alkylation reaction is preferably performed in a suitable inert solvent or diluent, for example N,N-dimethylformamide, N-methylpyrrolidin- 2-one, N,N-dimethylacetamide, dimethylsulphoxide, acetone, 1,2-dimethoxyethane or tetrahydrofuran, and at a temperature in the range, for example, −10° to 150° C., conveniently at or near ambient temperature.

Alternatively the starting material of the formula III wherein $R^2$ is fluoro may conveniently be prepared by the coupling reaction of an alcohol of the formula VI with a compound of the formula VII wherein $R^3$ and $R^4$ have any of the meanings defined hereinbefore. The coupling reaction is preferably performed in the presence of a suitable base as defined hereinbefore, in a suitable inert solvent or diluent as defined immediately hereinbefore other than acetone, 1,2-dimethoxyethane or tetrahydrofuran, and at a temperature in the range, for example, −10° to 100° C., conveniently in the range 20° to 40° C.

The preparation of an alcohol of the formula VI is described in European Patent Application No 0385662 A2 (corresponding to U.S. Pat. No. 5,134,148). A compound of the formula VII is prepared using methods analogous to those described in that same Application, or within European Patent Application No. 90306765.0 (published as European Patent Application No. 0409413; see, for example, Examples 1 and 19 thereof corresponding to U.S. Pat. No. 5,208,259). The preparation of an example of a starting material of the formula VII is described within the accompanying non-limiting Examples which are provided for the purpose of illustration only.

According to a further feature of the invention there is provided the use of a quinolinium salt of the formula I for the manufacture of a 1-alkyl-2-quinolone of the formula VIII wherein $R^1$, $R^2$, $R^3$ and $R^4$ have any of the meaning defined hereinbefore, which comprises the oxidation of said quinolinium salt of the formula I.

The oxidation may be performed by standard procedures of organic chemistry or utilising enzymatic methods, for example, by way of suitable oxidoreductase enzymes such as the quinine-oxidising enzyme of rabbit liver. Conveniently the oxidation may be performed by heating a mixture of the quinolinium salt of the formula I and an alkali metal or alkaline earth metal hydroxide such as sodium hydroxide or potassium hydroxide in the presence of air to a temperature in the range for example 20° to 300° C., preferably in the range 20° to 50° C.

The oxidation is preferably performed in the presence of an aqueous solution of a suitable base such as an aqueous solution of an alkali metal or alkaline earth metal hydroxide, for example, sodium hydroxide or potassium hydroxide, and using a mild oxidant such as an aqueous solution of a alkali metal or alkaline earth metal Fe(III) salt such as sodium or potassium ferricyanide. Alternative mild oxidants under such basic conditions include, for example, peroxides such as hydrogen peroxide and, for example, alkali metal or alkaline earth metal permanganates such as potassium permanganate. The reaction is conveniently performed in the presence of a suitable inert co-solvent or diluent such as toluene, 1,2-dimethoxyethane, tetrahydrofuran or 1,4-dioxan and at a temperature in the range, for example 0° to 100° C., conveniently in the range 20° to 70° C.

According to a further feature of the invention there is provided a process for the manufacture of a 1-alkyl-2-quinolone of the formula VIII wherein $R^1$, $R^2$, $R^3$ and $R^4$ have any of the meanings defined hereinbefore, which comprises:

(a) the reaction of a quinoline derivative of the formula III, wherein $R^2$, $R^3$, and $R^4$ have any of the meanings defined hereinbefore, with an alkylating agent of the formula $R^1$-X wherein $R^1$ and X have any of the meanings defined hereinbefore; and (b) the oxidation of the quinolinium salt of the formula I so obtained.

The alkylation and oxidation reactions of steps (a) and (b) respectively may be performed using the conditions described hereinbefore for the individual steps.

The quinolinium salts of the formula I are thus seen to be key intermediates in the preparation of 1-alkyl-quinolones of the formula VIII. Said quinolinium salts may readily be obtained in pure crystalline form from the quinoline derivatives of the formula III without the need of a chromatographic purification step and they may readily be converted to the required 1-alkyl-2-quinolone derivatives of the formula VIII which may also be isolated without the need of a chromatographic purification step.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–20° C. and under an atmosphere of an inert gas such as nitrogen or argon;

(iii) yields are given for illustration only and are not necessarily the maximum attainable;

(iv) the intermediates of the formula I and the end-products of the formula VIII have satisfactory microanalyses and their structures were generally confirmed by NMR and mass spectral techniques; and (v) melting points are uncorrected and were determined using a Merrier SP62 automatic melting point apparatus or an oil-bath apparatus; melting points for the intermediates of the formula I and for end-products of the formula VIII were determined after recrystallisation from a conventional organic solvent such as ethanol, methanol, acetone, ether or hexane, alone or in admixture.

EXAMPLE 1

A mixture of 6-[(3-fluoro-5-[4-methoxy-3,4,5,6-tetrahydro-2H-pyran-4-yl]phenoxy)methyl]quinoline (0.367 g), methyl iodide (0.2 ml) and acetonitrile (7 ml) was stirred at ambient temperature for 16 hours. The precipitate was filtered off to give 6-[(3-fluoro-5-[4-methoxy-3,4,5,6-tetrahydro-2H-pyran-4-yl]phenoxy)-methyl]-1-methylquinolinium iodide (0.29 g) in 57% yield, m.p. 190° C.

The 6-[(3-fluoro-5-[4-methoxy-3,4,5,6-tetrahydro-2H-pyran-4-yl]phenoxy)methyl]quinoline used as a starting material was obtained as follows:

A Grignard reagent was prepared from 3,5-difluorobromobenzene (38.6 g) and magnesium (4.88 g) in a mixture of toluene (100 ml) and tetrahydrofuran (50 ml) using the following method. The 3,5-difluorobromobenzene was dissolved in toluene (50 ml) and a portion (approx. 5%) of the solution was added to a stirred suspension of the magnesium in a mixture of toluene (50 ml) and tetrahydrofuran (50 ml). The mixture was stirred at ambient temperature for approximately 40 minutes until the initiation of the exothermic formation of the Grignard reagent was observed. The mixture was cooled in an ice-bath to a temperature in the range 15° to 20° C. while the remainder of the solution of 3,5- difluorobromobenzene was added. The mixture was stirred at ambient temperature for 2 hours.

3,4,5,6-Tetrahydro-2H-pyran-4-one (10.69 g) was added over 1 hour to a portion (100 ml) of the Grignard reagent so obtained which was cooled to a temperature in the range 15° to 20° C. The mixture was stirred at ambient temperature for 2 hours. The mixture was cooled in an ice-bath and aqueous hydrochloric acid solution (50% w/v, 25 ml) and brine (30% w/v, 52 ml) were added in turn. The toluene layer was separated and the aqueous layer was extracted with toluene (32 ml). The organic solutions were combined and washed with water (4×32 ml). The solution was evaporated under reduced pressure to a volume of 16.3 ml. There was thus obtained a concentrated (90% w/v) solution of 4-(3,5-difluorophenyl)-4-hydroxy-3,4,5,6-tetrahydro-2H-pyran in toluene. The concentrate was warmed to 60° C. and chlorobenzene (22.25 ml) was added, the temperature being maintained at 60° C. The mixture was allowed to cool to ambient temperature and then cooled in an ice-bath to a temperature in the range 0° to 5° C. The precipitate was isolated and washed with hexane (2×10 ml). There was thus obtained 4-(3,5-difluorophenyl)-4-hydroxy-3,4,5,6-tetrahydro-2H-pyran (12.2 g).

A portion (7.15 g) of the material so obtained was dissolved in N-methylpyrrolidin-2-one (25 ml) and added to a slurry of sodium hydride (60% w/w dispersion in mineral oil; 3.34 g) in N-methylpyrrolidin-2-one (32 ml) which was cooled in an ice-bath to approximately 20° C. The mixture was stirred at this temperature for 30 minutes. Methyl iodide (5.22 g) was dissolved in N-methylpyrrolidin-2-one (2 ml) and added to the mixture. The resultant mixture was warmed to 30° C. and stirred for 2 hours. There was thus obtained a solution of 4-(3,5-difluorophenyl)-4-methoxy-3,4,5,6-tetrahydro-2H-pyran in N-methylpyrrolidin-2-one which was used in the next step without being isolated.

Thus tert-butanol (3.71 g) in N-methylpyrrolidin-2-one (2 ml) was added over 1 hour to the solution of 4-(3,5-difluorophenyl)-4-methoxy-3,4,5,6-tetrahydro-2H-pyran and the mixture was stirred at a temperature of 25° C. for 1 hour. The mixture was cooled in an ice-bath to a temperature in the range 5° to 10° C. and a solution of 6-hydroxymethylquinoline [5.84 g; EP 0385662 A2, Ex 6(6), Note f. (corresponding to U.S. Pat. No. 5,134,148)] in N-methylpyrrolidin-2-one (30 ml) was added over 30 minutes. The mixture was stirred at ambient temperature for 16 hours and then poured into water (50 ml). Toluene (100 ml) was added and the mixture was acidified to pH 6 by the addition of glacial acetic acid (approx. 1.5 ml). The toluene layer was separated and the aqueous layer was extracted with toluene (100 ml). The organic solutions were combined and washed with water (100 ml) and with a saturated brine solution (100 ml). The resultant organic solution was evaporated and there was thus obtained 6-[(3-fluoro-5-[4-methoxy-3,4,5,6-tetrahydro-2H-pyran-4-yl]phenoxy)methyl]quinoline (7.35 g, 60%), m.p. 100° C.

NMR Spectrum (CDCl₃, delta values) 1.95(m, 4H), 2.96(s, 3H), 3.7(m, 4H), 5.24(s, 2H), 6.6–6.9(m, 3H), 7.43(m, 1H), 7.78(m, 1H), 7,89(m, 1H), 8.18(m, 2H), 8.95(m, 1H).

EXAMPLE 2

A mixture of 6-[(3-fluoro-5-[4-methoxy-3,4,5,6-tetrahydro-2H-pyran-4-yl]phenoxy)methyl]quinoline (0.367 g), methyl iodide (0.13 ml), toluene (1 ml) and acetonitrile (6 ml) was stirred at ambient temperature for 16 hours. The precipitate was filtered off to give 6-[(3-fluoro-5-[4-methoxy-3,4,5,6-tetrahydro-2H-pyran-4-yl]phenoxy)methyl]-1-methylquinolinium iodide (0.19 g) in 37% yield.

EXAMPLE 3

A mixture of 6-[(3-fluoro-5-[4-methoxy-3,4,5,6-tetrahydro-2H-pyran-4-yl]phenoxy)methyl]quinoline (1.835 g), dimethyl sulphate (0.52 ml) and methylene chloride (25 ml) was stirred and heated to reflux for 16 hours. The mixture was cooled to ambient temperature and the precipitate was filtered off to give 6-[(3-fluoro-5-[4-methoxy-3,4,5,6-tetrahydro-2H-pyran-4-yl]phenoxy)methyl]-1-methylquinolinium methyl sulphate (1.9 g) in 77% yield.

NMR Spectrum (CD₃OD, delta values) 1.90–2.05(m, 4H), 2.95(s, 3H), 3.65(s, 3H), 3.70–3.85(m, 4H), 4.70(s, 3H), 5.45(s, 2H), 6.75–6.85(m, 2H), 6.95(m, 1H), 8.00–8.10(m, 1H), 8.30–8.40(m, 1H), 8.45–8.55(m, 2H), 9.15–9.20(d, 1H), 9.30–9.35(d, 1H).

EXAMPLE 4

A mixture of a toluene solution of 6-[(3-fluoro-5-[4-methoxy-3,4,5,6-tetrahydo-2H-pyran-4-yl]phenoxy)methyl]quinoline (8% w/v, 115 ml) and dimethyl sulphate (4.75 g) was heated to 60° C. and stirred at this temperature for 4 hours. The mixture was cooled to ambient temperature and the precipitate was filtered off, washed with toluene (30 ml) and dried to give 6-[(3-fluoro-5-[4-methoxy-3,4,5,6-tetrahydro-2H-pyran-4-yl]phenoxy)-methyl]-1-methylquinolinium methyl sulphate (10.7 g) in 87% yield.

EXAMPLE 5

A solution of potassium ferricyanide (2.5 g) in aqueous sodium hydroxide solution (10% w/v, 7 ml) was added to a stirred slurry of 6-[(3-fluoro-5-[4-methoxy-3,4,5,6-tetrahydro-2H-pyran-4-yl]phenoxy)methyl]-1-methylquinolinium methyl sulphate (1 g) in 1,4-dioxan (7 ml) and the mixture was heated to 50° C. for 2 hours. Toluene (10 ml) was added and the phases were separated. The aqueous phase was washed with toluene (10 ml). The organic phases were combined, washed with water and evaporated. There was thus obtained 6-[(3-fluoro-5-[4-methoxy-3,4,5,6-tetrahydro-2H-pyran-4-yl]phenoxy)methyl]-1-methyl-2-quinolone (0.78 g) in 96% yield, m.p. 145–146° C. (recrystallised from a 1:1 v/v mixture of acetonitrile and water).

EXAMPLE 6

A solution of potassium ferricyanide (0.164 g) in aqueous sodium hydroxide solution (10% w/v, 8.4 ml) was added to a stirred slurry of 6-[(3-fluoro-5-[4-methoxy-3,4,5,6-tetrahydro-2H-pyran-4-yl]phenoxy)-methyl]-1-methylquinolinium methyl sulphate (1.2 g) in toluene (4.2 ml) and the mixture was heated to 60° C. for 3.5 hours. The phases were separated. The aqueous phase was extracted with toluene (2.1 ml) which had been warmed to 60° C. The organic phases were combined, washed with 2N aqueous hydrochloric acid and with water. The toluene solution was concentrated to a volume of 2.5 ml, warmed to 60° C. and petroleum ether (b.p. 100°–120° C.; 2.5 ml) was added. The mixture was allowed to cool to ambient temperature and then cooled to 0° C. for 1 hour. The precipitate was filtered off. There was thus obtained 6-[(3-fluoro-5-[4-methoxy- 3,4,5,6-tetrahydro-2H-pyran-4-yl]phenoxy)methyl]-1-methyl-2-quinolone (0.76 g) in 87% yield, m.p. 145.9° C. (recrystallised from a 1:1 v/v mixture of acetonitrile and water; the resultant crystals being recrystallised from a 9:1 v/v mixture of ethanol and methanol).

CHEMICAL FORMULAE

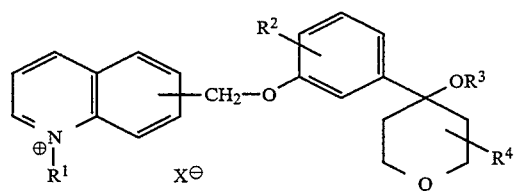
I

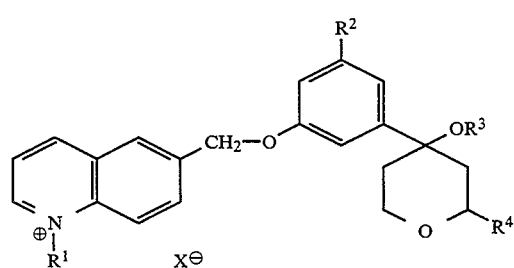
II

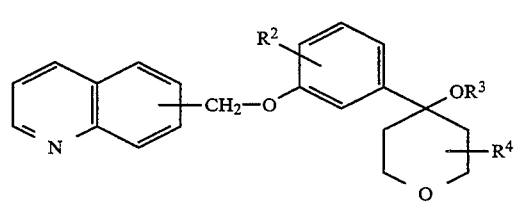
III

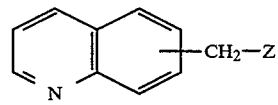
IV

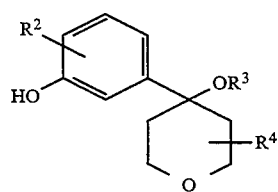
V

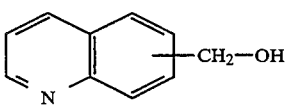
VI

-continued
CHEMICAL FORMULAE

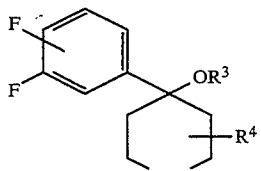
VII

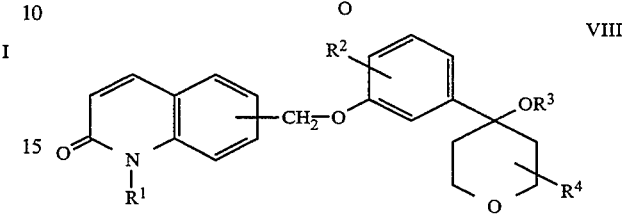
VIII

What we claim is:

1. A crystalline quinolinium salt of the formula I

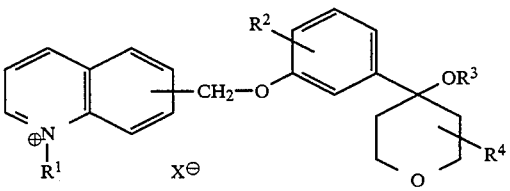
I wherein $R^1$ and $R^3$ which may be the same or different each is (1-4C)alkyl;
$R^2$ is hydrogen or fluoro;
$R^4$ is hydrogen or (1-4C)alkyl; and
$X^\ominus$ is bromide, iodide or (1-4C)alkyl sulphate.

2. A crystalline quinolinium salt of the formula II

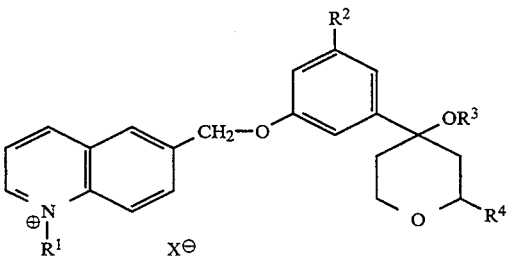
II wherein $R^1$ is methyl or ethyl;
$R^2$ is hydrogen or fluoro;
$R^3$ is methyl;
$R^4$ is hydrogen or methyl; and
$X^\ominus$ is iodide or methyl sulphate.

3. A crystalline quinolinium salt selected from: 6-[(3-fluoro-5-[4-methoxy-3,4,5,6-tetrahydro-2H-pyran-4-yl]phenoxy)methyl]-1-methylquinolinium iodide and 6-[(3-fluoro-5-[4-methoxy-3,4,5,6-tetrahydro-2H-pyran-4-yl]phenoxy)methyl]-1-methylquinolinium methyl sulphate.

* * * * *